United States Patent
Stach et al.

(10) Patent No.: US 6,405,539 B1
(45) Date of Patent: Jun. 18, 2002

(54) METHOD AND DEVICE FOR RECOVERING GASES

(75) Inventors: Helmut Stach, Berlin; Hans-Juergen Bachert, Schulzendorf; Hartmut Welke, Ahrensfelde, all of (DE)

(73) Assignee: Pneumatic Berlin GmbH, Berlin (DE)

( * ) Notice: Subject to any disclaimer, the term of this patent is extended or adjusted under 35 U.S.C. 154(b) by 0 days.

(21) Appl. No.: 09/530,576

(22) PCT Filed: Nov. 3, 1998

(86) PCT No.: PCT/DE98/03260

§ 371 (c)(1),
(2), (4) Date: Jul. 5, 2000

(87) PCT Pub. No.: WO99/22845

PCT Pub. Date: May 14, 1999

(30) Foreign Application Priority Data

Nov. 4, 1997 (DE) .......................... 197 49 963
Oct. 9, 1998 (DE) .......................... 198 47 950

(51) Int. Cl.$^7$ .............................................. F25B 21/02
(52) U.S. Cl. .................................................. 62/3.4
(58) Field of Search ........................ 62/3.2, 3.4; 95/11, 95/17, 87; 96/109, 113

(56) References Cited

U.S. PATENT DOCUMENTS

| | | | |
|---|---|---|---|
| 3,592,191 A | | 7/1971 | Jackson |
| 4,772,296 A | * | 9/1988 | Potts ............................. 55/67 |
| 5,201,182 A | * | 4/1993 | Grignon et al. ............... 62/3.2 |
| 5,242,403 A | * | 9/1993 | Falb et al. .................... 604/113 |
| 5,287,702 A | * | 2/1994 | Blackshaw et al. ........... 62/3.2 |
| 5,413,166 A | * | 5/1995 | Kerner et al. ................. 165/30 |
| 5,417,742 A | | 5/1995 | Tamhankar et al. |
| 5,465,578 A | * | 11/1995 | Barben et al. ................. 62/3.2 |
| 6,110,257 A | * | 8/2000 | Tom .............................. 95/22 |

FOREIGN PATENT DOCUMENTS

| | | |
|---|---|---|
| DD | 239 947 A1 | 10/1986 |
| DE | 36 28 858 A1 | 3/1988 |
| DE | 37 13 346 A1 | 11/1988 |
| DE | 37 31 688 A1 | 3/1989 |
| DE | 40 03 668 A1 | 8/1990 |
| DE | 42 33 577 A1 | 4/1994 |
| DE | 44 06 766 A1 | 9/1994 |
| DE | 44 06 776 A1 | 1/1996 |
| DE | 195 31 933 A1 | 2/1997 |
| DE | 195 32 500 A1 | 3/1997 |
| DE | 195 49 271 A1 | 7/1997 |
| EP | 0 284 227 A2 | 9/1988 |

OTHER PUBLICATIONS

Wilhelm Otten, et al., "Einsatzmöglichkeiten hydrophober Zeolithe in der Adsorptionstechnik", Chem-Ing.–Tech. 64, Nr. 10, pp. 915–925, 1992.

Registration Document of a Utility Model No. 297 20 026.7 Owner = Pneumatik Berlin GmbH. Date of Application = Nov. 4, 1997. Date of Publication = Apr. 16, 1998.

* cited by examiner

*Primary Examiner*—Henry Bennett
*Assistant Examiner*—Melvin Jones
(74) *Attorney, Agent, or Firm*—Oblon, Spivak, McClelland, Maier & Neustadt, P.C.

(57) ABSTRACT

The invention relates to a method and apparatus for selectively removing and recovering gas and steam mixtures which can be used in different technical fields, in particular in the medical field such as anesthetics. Individual components of the mixtures are bound in adsorbing substances while other components pass these. The adsorbed gas is desorbed by way of heating up the adsorbing substances, is liquified in a following condensor and fed for reuse. For the desorbing substances zeolites are used which have been adapted by synthesis or modification for the application purpose, in particular dealuminated zeolites.

8 Claims, 1 Drawing Sheet

METHOD AND DEVICE FOR RECOVERING GASES

TITLE OF THE INVENTION

BACKGROUND OF THE INVENTION

1. Field of the Invention

The present invention relates to a method and apparatus for recovering gases. The areas of application are the anesthetic gases used in human and veterinary medicine as well as the recovery of gases from expired air. The apparatus allows the intermediate storage of gases in appropriate zeolites and the complete recovery of the gases from the gas mixtures produced during the application by way of a thermally induced expulsion from these zeolites.

2. Discussion of the Background

There are known apparatuses with whose help gas mixtures, during their introduction into defined chemical substances, are split up in such a way that the desired separation is carried out mostly by a chemical reaction. In this way, new compounds arise which are either disposed of in their present form or are stored over a long period of time however, in most cases these compounds are very difficult to recover. Examples of adsorptive gas cleaners based on the principal of flow through a suitable chemically active liquid are the so-called scrubbers as are found in the semiconductor industry in applications with highly toxic process gases, or also different types of dry bed absorbers whose active components can be optimized for the different kinds of gases to be separated. All these arrangements show the same disadvantage in that they are not equipped for economically recovering the gases adsorbed in these devices. It is equally commonly know that besides the known absorption which takes place in suitable liquids and solid materials, microporous solid-state bodies such as zeolites, active carbon among others, can adsorb certain materials while heat energy is given off and can desorb certain materials while heat energy is being received. Similar process take place during the physical state changes of matter (e.g., ice-water-vapor).

The prior art presents a number of publications for sorption of the different kinds of gases in liquids, solid absorbers but also zeolites and other micro-porous solid-state bodies. Filters for gas masks likewise absorb and adsorb completely the harmful substances until a saturation limit is reached. Beyond this limit it is relatively easily controllable that the substances will go through practically uninfluenced. This means that a limit point is always set-up for the adsorbed gases e.g. anesthetic gases in which the sorbents and the sorptives are equally balanced. This point is substantially dependent upon the pressure and temperature of the components.

The technical, physical and chemical prerequisites for the highest possible sorption capacity together with an optimal regeneration ability of the sorption equipment are described in the patent documents DE 3731688, DE 3628858 and DD 239947. Documents DE 4003668 and DE 3713346 report on the removal of halogenated carbon hydroxides by means of zeolites. Described in the published document DE 19549271 is a method in which silicium rich zeolites are employed for recovering gases with different vapor pressures from gas mixtures. In this document no information is given about the Si/Al ratio. Zeolites are suitable as well for removing substances from watery solutions (DE 44 06776 and DE 19531933). Recently, in particular reduced aluminium and dealuminated zeolites have found use as an adsorption means as can be taken from patent document DE 19532500; Document DE 4233577 describes the sorption of halogenated carbon hydroxides onto dealuminated zeolites.

The known commercially used arrangements show the common feature that either the substances isolated by the sorption process stay put and are disposed together with the sorbents, for example in appropriate combustion plants, or also taking the chemical path are changed into relatively harmless products and are then deposited. In this way, among others certain gas masks are filled with sorbents consisting mostly of modified active carbon.

U.S. Pat. 3,592,191 reports on the recovery of anesthetic gases with absorbing material. At the same time the water vapour is bound by means of a hydroscopic material.

Otten, Gail and Frey (Chem.-Ing.-Tech. 64 (1992) No. 10, 915–25) present a dealuminated Y-zeolite having a $SiO_2/Al_2O_3$ ratio of over 200 suitable for cleaning expired air and recovering solvents e.g. from toluene. These high dealuminated zeolites show however still a good adsorption ability for polar substances. Patent EP 0284227 describes an apparatus and method in which alumosilicates can absorb up to 15 percent-by-weight of anesthetic gases having relatively small molecule diameters. In the method presented there a recovery is also suggested in such a way that a carrier gas which has been heated up flows through the filled adsorber, brings a greater part of the adsorbed gases to be desorbed and by a subsequent cooling down to low temperatures which are gained from vaporizing liquid nitrogen, can condense again in a suitable container and thereby be led to reuse. Employed are zeolites having a $SiO_2/Al_2O_3$ ratio greater than 50. The recovery rate in this method lies considerably under 50%; no statement is made on the quality of the recovered gases. In this method sevolfluran is not separated. Since the alumosilicates used in this patent however comprise of a relatively high share of aluminium which is known for its catalytic activity with the anesthetic gases being considered which are all halogenated carbon hydrides, a direct reuse does not appear possible in view of the expected catalytic resultant products. The necessarily high temperature for desorption by means of hot carrier gases increase this effect even more.

SUMMARY OF THE INVENTION

The almost complete recovery of anesthetic gases has not yet been described.

The object of the invention is to provide a method and apparatus for the sorption of principally gaseous substances, for example, anesthetic gases, and which allow to make it possible to almost completely recover these substances, for example, to recover the substances in air expired from the patient for the purpose of saving costs or to relieve the environment while requiring the least possible amount of energy and having the least affect on the composition of the anesthetic gases.

This object is satisfied in that by making use of desorption processes adapted in a suitable way, individual components of the mixture are bound above a temperature specific to the substance in adsorbing zeolites while other components pass these zeolites wherein the adsorbed gas is desorbed by way of heating up the adsorbing substances, is liquified in a following condenser and is fed for reuse.

DETAILED DESCRIPTION OF THE INVENTION

Figure 1:
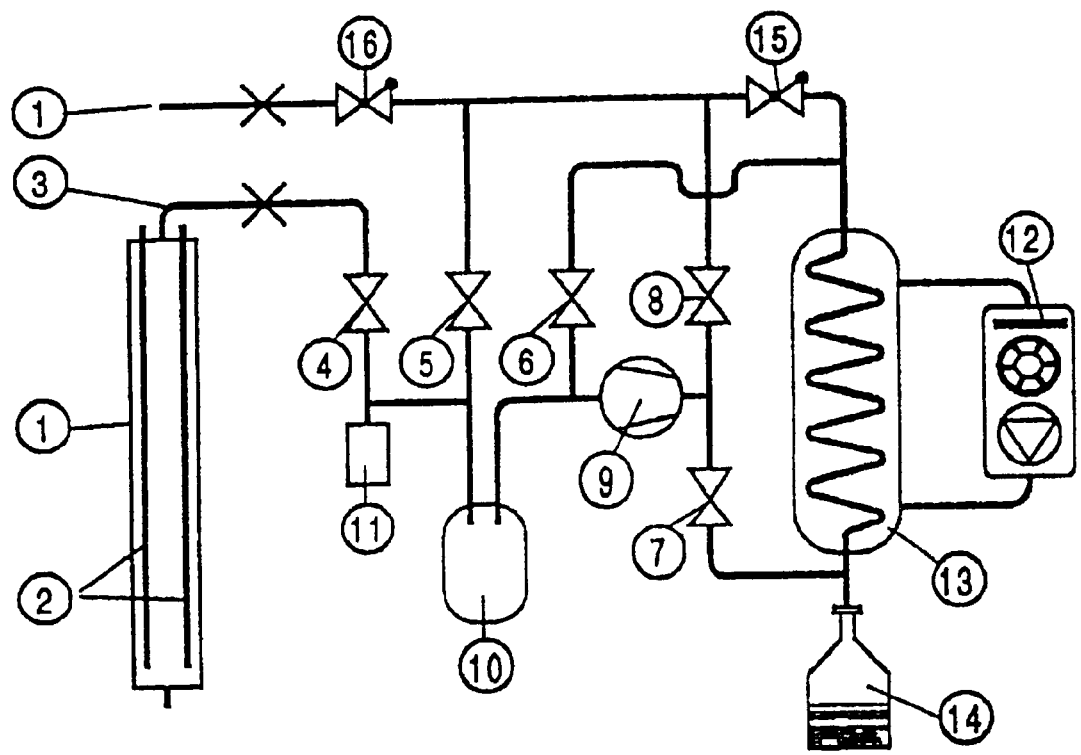
FIG. 1 shows an apparatus for the recovery of the gases.

According to the invention silicon rich zeolites are used as an adsorption means having:

a) an extremely high Si/Al ratio of greater than 180:1 (corresponds to a —$SiO_2/Al_2O_3$ ratio of 360:1) which lessens the catalytic reactions with the anesthetic gas;
b) a considerably reduced adsorbing heat; the value of adsorbing heat determines the desorption temperature which should be as low as possible in order to avoid catalytic reactions;
c) an adsorption capability for all presently used inhalant anesthetics;
d) a greater adsorption capability for anesthetic gases;
e) deformed zeolite material (hollow body having deviations up to 10 mm) whereby the flow characteristics are changed due to the larger secondary pore system and with it the adsorption capability and the adsorption kinetic are positively influenced;
f) a pore diameter of around 0.7 nm; and
g) hydrophobic and organophilic character which have a small or no electrostatic field in the pores and hollow spaces.

Surprisingly it has emerged that the solution of the invention almost shuts out a catalytic reaction with the anesthetic gas and allows its reuse or new manufacture. The method and apparatus according to the invention have the following advantages:

no or very little adsorption or adsorption removable by simple rinsing steps from air, laughing gas, carbon dioxide, water vapour, large adsorption capability for the known anesthetic gases in particular Halothan, Isofluran, Sevofluran, Desfluran and Enfluran, lowest possible catalytic reaction with fluorinated carbon hydrides in order to allow either direct reuse or a cost favourable reprocessing and new manufacture, energically favourable operation by omission of transport gases whose mass amounts to a multiple of the gases to be recovered, use of a cooling system requiring no other connections other than electric.

The method and apparatus allow the complete recovery of the corresponding gases.

The apparatus for sorption and recovery is made up of an adsorber 1 with integrated heating elements 2, which collects the gas mixture to be disposed of by way of appropriate gas technical connections with the given outgoing air system. In the case of recovery the zeolite present in the adsorber and warmed up by the heater 2 is desorbed via the connecting lead 3 and the valve 4 at low pressure with the help of a chemical vacuum pump 9. Possible few components of the gas having a higher boiling point, mostly water, will be taken up in the prefractionator 10. The vacuum pump not only serves to support the desorption but rather effects mainly a reduction in the thermal strain of the desorption process in order to prevent a decomposition of the inhalant anesthetics. The chemical vacuum pump guarantees the purity of the condensed products and allows good yields. The prefractionator does not just separate the water but rather lessens a possible adsorption of the nitrous oxide (laughing gas) available in the expired air which is in greater surplus compared to anesthetic gas.

The necessary pressure which is determined by the efficiency of the pump 9, the temperature of the heating elements 2, the mass of the zeolite in adsorber 1 and its condition as well as the actual degree of its load with a given anesthetic gas, is detected by pressure sensor 11 and is controlled by suitably positioning the valves 5 and 6 in conjunction with an electronic control such that an optimal condensation in the condensor 13 is possible to which the desorbed gas is lead via valve 7. The required temperature of the condenser 13 is made available by a cooling aggregate 12 having air cooling Peltier elements and is adjusted to the optimal temperature between −5 and +10×C depending on the anesthetic gas. The arrangement of the Peltier cooling (see FIG. 1) is completely abnormal since there is no direct cooling of the condensor area but rather a cooling of the coolant circulation is carried out. This arrangement was chosen in order to achieve a quick cooling and to be able to adapt the cooling temperature to the different vapour pressures of the different anesthetic gases.

The return valves 15 and 16 allow complete separation of the equipment and the pressure control system from the surrounding atmosphere so that almost 100% condensation of the desorbing gas is possible. The arrangement of the valves corresponds to a safety measure since any emerging concentrated anesthetic gas would bring danger to the personal and the environment. Therefore the whole system is also operated under low pressure (see FIG. 1) and two return valves are used. The pressure sensor is connected between the two valves. By suitably positioning of the valves 4 to 8 it is moreover possible with the help of the vacuum pump 9 to vapourise any condensation residue which might arise or also small amounts of water arising from the previous processes and thereby clean the whole system. The container 14 for collecting condensed material collects the recovered anesthetic gas and can be the container used by the manufacturer for the anesthetic gas in order to avoid any mix up. Apparatuses for measuring temperature, means for controlling amounts of gas and control electronics for valves, temperatures and pressure are not shown.

The apparatus is intended preferably for separating and recovering anesthetic gases from exhaust systems in the medical anesthetics.

For this purpose the adsorber 1 can also be used in a reciprocating manner, for sorption(depositing) of the anesthetic gases, or with the help of an appropriate temperature/time cycle, for desorption with temperatures up to maximum 150×C, whereby in a known way the adsorped gas is again expelled and with open valves 4 and 7 is condensed in a condensor 13 and stored in condensed material container 14. After the external feeding of energy has been interrupted the apparatus with valves now closed is prepared for a new process pass and can cool down to the temperature of the environment whereafter the adsorber can be separated and used again for sorption of anesthetic gas as well as when the need arises a second adsorber can now be desorbed.

The adsorbers filled with zeolite and used for the mentioned intermediate storage are not necessarily integrated in the actual recovery system but rather are employed as freely movable adsorbers so that a system having appropriate dimensioning can also cooperate with several adsorbers.

The described apparatus can be used sationary or also mobile and in addition to the recovery of anesthetic gases also for recovering other gases which are either harmful to the environment and/or are expensive.

The crux of the invention lies in the combination of known elements and new ways of solving the task which mutually influence the other, and in its new overall effect bring advantages in its employment and the strived success which lies in the fact that now a complete recovery of the corresponding gases is possible.

The manner in which the apparatus functions will be explained in more detail by way of an example of an embodiment without restricting it to this example.

EXAMPLE OF AN EMBODIMENT

For the purpose of the invention being used in association with an anesthetic device a stationary apparatus will be described. Under the assumption that during an operational cycle of maximum 8 h an anesthetic gas mixture is employed, for example nitrous oxide (laughing gas) and oxygen (2/1, Vol./Vol.) having a flow rate of 1.5 l/min, wherein 6 percent-by-volume Desfluran is contained therein, when the special zeolite e.g. dealuminated Faujasite is used then a mass of around 3 kg is needed in order to bind the mentioned Desfluran amount of around 0.33 kg in the adsorber I at room temperature. Since this mass corresponds roughly to the amount contained in a usual Desfluran bottle which comes for use in the anesthetics and depending on the applied anesthetic method sometimes more or sometimes less patients swill be taken in the medium term, the adsorber can adsorb roughly the capacity of a Desfluran bottle and according to this assumption will be connected to the connector lead 3 of the apparatus for starting the recovery process. Since all the components of the apparatus are carried out vacuum tight, after the one-sided closing of the adsorber the following process will take place (FIG. 1).

First of all, by switching on the pump 9 and opening the valves 6 and 8, possible residue from the previous process will be vapourised from the condensor 13, the condensed material collector container 14 and the connecting leads and then removed from the system via the return valve 16. After the cooling aggregate 12 has cooled the condenser 13 to the necessary condensation temperature, the valves 6 and 8 are closed and the valves 4 and 7 are opened. This results in a vacuum in adsorber 1 which can be evaluated by pressure sensor 11 and which leads to the desorption starting and a corresponding mass can be caught in container 14. Since the velocity of the condensation is also dependent on the mass transport through the pump 9 and with it the partial pressure of the anesthetic gas in the adsorber 1, this pressure by way of a gradual increase in temperature of the zeolite with the help of the heater 2 is kept so long constant in the further course of the recovery process until the maximum temperature is reached and the partial pressure above the zeolite decreases with progressive desorption. The end of the process is reached when despite high temperature the pressure in the adsorber 1, also without the pump 9 controlled with help from the pressure sensor 11, remains over a long time at around 10 mbar. Under these conditions, the rest mass of the anesthetic gas remaining in adsorber 1 lies under 1 g, that is around 0.1 percent-by-weight.

On average almost 100% of the anesthetic gas emitted from the patients is adsorbed and over 90% recovered. Depending on whether the anesthetist uses higher or lower concentrations of anesthetic then of course the amount of anesthetic gas emitted from the patient during an anesthetic which can thus be absorbed will vary. In every case investigated here the recovery rate, as compared with a full amount of anesthetic gas, lay however over 60% and therefore twice as high with silicate. Gas chromatography investigations on the purity of the recovered gases resulted in a purity between 98.0 and 99.7%. The results show that rather gas feeding elements not yet optimized are responsible as main components for the small amounts of unclean rest. When Isofluran is used the concentration applied is typically lower which results in roughly a factor of 6 more application time for the adsorber until desorption for the same degree of adsorption.

REFERENCE NUMERAL LIST 1 adsorber
2 heater
3 gas connecting lead
4 valve
5 valve
6 valve
7 valve
8 valve
9 chemical vacuum pump
10 prefractionator
11 pressure sensor
12 peltier cooling aggregate
13 condenser
14 condensed material collecting container
15 return valve
16 return valve

What is claimed is:

1. Method for removing and recovering gases having different steam pressures from gas mixtures in which individual components from the mixture are bound above a temperature specific to the substance in absorbent zeolites while other components pass the zeolites, wherein the adsorbed gas is desorbed by heating the adsorbing substances then liquified in a condenser and fed for reuse, wherein the zeolites are Si-rich zeolites having a Si/Al ratio greater than 180 and a pore diameter of about 0.7 nm.

2. Method according to claim 1, wherein the zeolites possess a hydrophobic and organophilic character and show a small or no electrostatic field in the pores and hollow spaces.

3. The method according to claim 1, wherein the zeolites are made out of deformed zeolite material in the form of hollow bodies up to 10 mm.

4. Apparatus for carrying out the method according to claim 1 having an adsorber (1) for collecting the emitted gas, said adsorber being connected via a connecting lead (3) and valves (4 and 7) to a chemical vacuum pump (9) which in turn feeds the gas which has been desorbed through low pressure and heating up with heater (2) to a condenser (13) kept at a suitable temperature by a cooling aggregate (12) whereby the gas is liquified and collected in a condensed material collection container (14), wherein Si-rich zeolites are used for the adsorber having a Si/Al ratio greater than 180 and a pore diameter of about 0.7 nm.

5. Apparatus according to claim 4, wherein a prefractionator (10) is filled with material made out of hydrophilic zeolite whose pore diameter is smaller than the diameter of the gases to be considered for recovery and which can be desorbed with thermal assistance outside or within the system.

6. The apparatus according to claim 4, wherein by means of the valve (5) controlled by a pressure sensor (11) and a suitable arrangement of the return valves (15 and 16), gas which has not condensed is fed back to the condenser.

7. Apparatus according to claim 4, wherein a Peltier cooler is used for the cooling aggregate (12).

8. The method of claim 1, wherein said gases are anesthetic gases; and wherein said method is performed in an apparatus having an adsorber (1) for collecting the emitted gas, said adsorber being connected via a connecting lead (3) and valves (4 and 7) to a chemical vacuum pump (9) which in turn feeds the gas which has been desorbed through low pressure and heating up with heater (2) to a condenser (13) kept at a suitable temperature by a cooling aggregate (12), whereby the gas is liquified and collected in a condensed material collecting container (14), wherein Si-rich zeolites are used for the adsorber having a Si/Al ratio greater than 180 and a pore diameter of about 0.7 nm.

* * * * *

UNITED STATES PATENT AND TRADEMARK OFFICE
CERTIFICATE OF CORRECTION

PATENT NO. : 6,405,539 B1
DATED : June 18, 2002
INVENTOR(S) : Helmut Stach et al.

It is certified that error appears in the above-identified patent and that said Letters Patent is hereby corrected as shown below:

Column 2,
Line 32, "sevolfluran" should read -- Sevofluran --

Column 4,
Line 55, "sationary" should read -- stationary --

Signed and Sealed this

Twenty-fifth Day of February, 2003

JAMES E. ROGAN
*Director of the United States Patent and Trademark Office*